United States Patent [19]

Schmolka

[11] Patent Number: 4,495,169
[45] Date of Patent: Jan. 22, 1985

[54] AEROSOL GEL SHAVING CREAM

[75] Inventor: Irving R. Schmolka, Grosse Ile, Mich.

[73] Assignee: BASF Wyandotte Corporation, Wyandotte, Mich.

[21] Appl. No.: 525,147

[22] Filed: Aug. 22, 1983

[51] Int. Cl.³ .................. A61K 7/00; A61K 7/15; A61L 9/04
[52] U.S. Cl. ............................ 424/47; 424/45; 424/73; 424/DIG. 13; 424/78
[58] Field of Search .............. 424/45, 47, 73, 78, 424/DIG. 13; 222/4, 394, 402.1

[56] References Cited

U.S. PATENT DOCUMENTS

| | | | |
|---|---|---|---|
| 3,476,853 | 11/1969 | Jatul et al. | 424/45 |
| 3,579,465 | 5/1971 | Schmolka | 252/316 |
| 3,639,575 | 2/1972 | Schmolka | 424/DIG. 13 X |
| 3,740,421 | 6/1973 | Schmolka | 424/65 |
| 3,748,276 | 7/1973 | Schmolka | 252/316 |
| 3,751,562 | 8/1973 | Nichols | 424/45 |
| 4,001,391 | 1/1977 | Feinstone et al. | 424/45 |
| 4,293,542 | 10/1981 | Lang et al. | 424/47 |
| 4,360,451 | 11/1982 | Schmolka | 424/78 X |
| 4,376,764 | 3/1983 | Schmolka | 424/78 |

FOREIGN PATENT DOCUMENTS 1444334  7/1976  United Kingdom .

Primary Examiner—Sidney Marantz
Assistant Examiner—Shawn P. Foley
Attorney, Agent, or Firm—Bernhard R. Swick

[57] ABSTRACT

A pressurized shaving cream composition in an aerosol container and adapted to form a spray upon release of pressure therefrom which composition is a liquid inside the container and forms a gel on contact with living tissue comprising water, volatile solvent, propellant and a polyoxyethylene-polyoxypropylene copolymer. The preferred composition also includes a volatile solvent and may advantageously include a treatment agent and conventional additives.

19 Claims, No Drawings

AEROSOL GEL SHAVING CREAM

BACKGROUND OF THE INVENTION

1. Field of the Invention

The present invention relates to a sprayable aerosol shaving composition which is a liquid in the aerosol container and forms a gel upon application to the skin.

2. Prior Art

The preparation of aqueous gels employing as gelling agents polyoxyethylene-polyoxypropylene block copolymers is well known to those skilled in the art and is taught in several patents including U.S. Pat. No. 3,740,421. It is also known in the art to apply such compositions by the use of aerosol-type containers. However, filling an aerosol container with a gel presents problems.

U.S. Pat. No. 3,751,562, issued Aug. 7, 1973, to Nichols, discloses an aerosol gel formulation employing an oxyethylated fatty alcohol, mineral oil, iodine and water.

U.S. Pat. No. 4,293,542, issued Oct. 6, 1981, to Lang et al, discloses aerosol formulations which can be an aqueous gel containing oxyethylated fatty alcohols and a gel-forming agent and, as an essential component, a pyridine derivative.

British Pat. No. 1,096,357 discloses an aerosol gel comprising a partial fatty acid soap of a polyvalent metal hydroxide, and a nonpolar oil along with propellants.

British Pat. No. 1,444,334 discloses an aerosol gel composition which may be employed as a shaving cream composition and which contains as a gelling agent a polyoxypropylene-polyoxyethylene block copolymer. The composition also includes a water-soluble soap. This patent is concerned with the problem of expelling a gel from an aerosol container and particularly avoiding cavitation around the dip tube as can be seen from column 2 thereof.

Co-pending U.S. patent applications Ser. Nos. 513,439, 525,148 and 524,985 disclose aerosol gel compositions which are liquid in the aerosol can and form a gel upon application to the skin.

SUMMARY OF THE INVENTION

The cavitation problem discussed in British Pat. No. 1,444,334 as well as filling problems are overcome in accordance with the instant invention by the use of a pressurized composition which may be sprayed from an aerosol container and which is liquid inside the container and forms a gel on contact with living tissue such as the skin of a human when the shaving cream is applied. This is accomplished by the combination of water, propellant, volatile solvent and certain polyoxyethylene-polyoxypropylene block copolymers. As employed throughout the instant specification and claims, the term "solvent" means a solvent for the gel composition of this invention. The water/copolymer ratio for the shaving creams of this invention should be less than 4.5:1. The volatile solvent evaporates upon contact with body heat whereby the liquid becomes a foamy gel.

DESCRIPTION OF THE PREFERRED EMBODIMENTS

The aerosol composition of the instant invention comprises by weight about 35 to 85 percent water, about 3 to 50 percent propellant, about 10 to 25 percent of the polyoxyethylene-polyoxypropylene copolymer and about 1 to 10 percent of the volatile solvent. The water/copolymer ratio is less than 4.5:1 with a preferred minimum ratio of 0.2:1. The composition may also include 0 to about 10 percent, preferably about 0.05 to 5.0 percent, of a treatment agent such as a beard softener or skin treatment agent, and 0 to 20 percent, preferably 1 to 10 percent of adjuvants.

The polyoxyethylene-polyoxypropylene block copolymer of use in the invention is a cogeneric mixture of conjugated polyoxyethylene-polyoxypropylene compounds corresponding to the following formula:

$$Y[(C_3H_6O)_n(C_2H_4O)_mH]_x \qquad (I)$$

wherein Y is the residue of an organic compound having from about 1 to 6 carbon atoms and containing x reactive hydrogen atoms in which x has a value of at least about 1, n has a value such that the molecular weight of the polyoxypropylene hydrophobe base is about 2250 to 7500 and m has a value such that the oxyethylene groups constitute about 45 to 90 weight percent of the compound. Falling within the scope of the definition for Y are, for example, propylene glycol, glycerine, pentaerythritol, trimethylolpropane, ethylene diamine and the like. The oxypropylene chains optionally, but advantageously, contain small amounts of oxyethylene and oxybutylene groups and the oxyethylene chains also optionally, but advantageously, contain small amounts of oxypropylene and oxybutylene groups. These compositions are more particularly described in U.S. Pat. Nos. 2,677,700, 2,674,619 and 2,979,528.

Nonionics which are particularly applicable are those in which Y is a propylene glycol residue, wherein the resulting formula is:

$$HO(C_2H_4O)_m(C_3H_6O)_n(C_2H_4O)_mH \qquad (II)$$

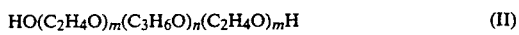

wherein n has a value such that the polyoxypropylene hydrophobe has a molecular weight of about 2250 to 4500 and m is the same as for formula (I).

Additional nonionics of particular value are those wherein Y is an ethylene diamine residue and the resulting formula is:

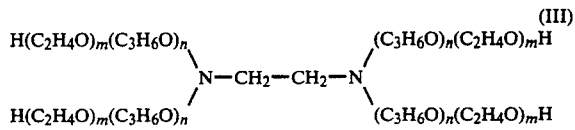

wherein n has a value such that the hydrophobe has a molecular weight of about 3500 to 7500 and m is the same as in formula (I) above.

A composition which is a liquid inside the container and forms a gel on contact with living tissue is achieved by including a volatile solvent in the composition. Such solvents include alcohols such as methyl, ethyl and propyl, ketones such as acetone, ethers such as methyl, ethyl, methyl-ethyl, and similar ethers, and alkyl chlorides such as dichloromethane. Non-volatile solvents such as liquid polyethylene glycols, propylene glycol, and dipropylene glycol, etc. can be employed together with the volatile solvent provided the mixture is homogenous. A shaving cream gel composition which includes such volatile solvent should have a water/- copolymer ratio of less than 4.5:1. The preferred minimum ratio is about 0.2:1.

The propellants can be any one or a blend of the following, as examples: propane, isobutane and other petroleum distillates, nitrogen, carbon dioxide, dimethylether, methylethylether, methylene chloride, vinyl chloride and fluorochlorohydrocarbons. The latter include Freon 115 pentafluorochloroethane and Freon C-318, octafluorocyclobutane.

A shaving cream composition would desirably contain at least one beard softener and/or skin treating agent which, when included would generally be in an amount of about 0.05 to 10 percent by weight. However, the polyoxyethylene-polyoxypropylene block copolymer may serve as the agent for wetting the chin and the beard whereby an additional agent would not be needed. If a high-foaming oxyalkylene copolymer is selected which has a polyoxypropylene hydrophobe molecular weight of about 2250 to 7000 and the oxyethylene groups constitute about 70 to 80 percent of the total molecular weight of the compound, it alone would serve as the foaming agent. If the polyoxyethylenepolyoxypropylene copolymer is a low-foaming copolymer, the shaving cream may also contain a small amount of a foaming agent, which may be nonionic, anionic, or amphoteric. Nonionics include high-foaming ethylene oxide adducts such as fatty alcohol ethoxylates and the anionics include sodium lauryl sulfate and lauryl ether sulfates. The propellant may also serve as a foaming agent eliminating the need for an additional foaming agent. Other examples of such foaming agents are triethanolamine lauryl sulfate, sodium dodecyl benzene sulfonate, water-soluble polyoxyethylene ethers of alkyl-substituted phenols, amine oxides, phosphate ester based surfactants, and water-soluble polyoxyethylene lauryl or dodecyl ethers. Numerous anionic and nonionic wetting agents suitable for the purposes of the present invention are described in detail in McCutcheon's "Emulsifiers and Detergents," 1982. Such agents could be included in amount of about 0.1 to 2.0 percent by weight.

Many and various adjuvants are generally also included in the these shaving cream gels. These could include proteins, amino acids, electrolytes and other ingredients normally found in body fluids. Humectants, such as propylene glycol or glycerine, may also be included. Further adjuvants could include silicone oils. Also, other adjuvants which impart further desired qualities to the skin may be incorporated in the compositions of the invention, e.g., skin fresheners or lather stabilizers or the like such as lanolin or its derivatives, lecithin, higher alcohols, dipelargonate esters or ethers, coconut oil and other fatty esters, and mixtures thereof may generally be used in minor proportions. Furthermore, coloring materials such as dyes and perfumes may be used, if desired. The amount of such adjuvants would range from 0 to about 20.0 percent by weight and preferably from about 1.0 to 5.0 percent by weight.

The following examples are included to further illustrate the present invention. Unless otherwise stated throughout the application, all parts and percentages are by weight and all temperatures are in degrees centigrade.

EXAMPLE 1

A concentrate is prepared from 20 parts of a polyoxyethylene-polyoxypropylene block copolymer of the type shown in formula (II) above, designated herein as copolymer #1, having a polyoxypropylene hydrophobe molecular weight of 4000 and containing oxyethylene groups in amount of 70 percent of the total copolymer weight, 3 parts propylene glycol and 77 parts water. Fifty-two parts of this gel concentrate and 6 parts of isopropanol are placed in an aerosol container. Thirty-five parts by weight of dimethylether propellant are then added through the valve. The contents when shaken and sprayed onto the face of an individual needing a shave forms a coating which becomes a foamy gel as the alcohol and propellant evaporate. This gel has good shaving characteristics and does not irritate the skin.

EXAMPLE 2

Example 1 is repeated substituting for copolymer #1 a polyoxyethylene-polyoxypropylene copolymer of the type shown in formula (III) above, referred to herein as copolymer #2, having a hydrophobe molecular weight of 7000 and containing oxyethylene groups in an amount of 80 percent of the total copolymer weight. When sprayed from the aerosol container onto the face of an individual needing a shave, a coating is formed which becomes a foamy gel as the solvent and propellant evaporate. This gel has good shaving characteristics and does not irritate the skin.

EXAMPLES 3-8

Six solutions are made up from all the components excluding the propellants of each of the example compositions set forth below and each placed in its individual aerosol container. The container is sealed with a valve and the respective propellant added through the valve. The contents of each when shaken and sprayed onto the face of an individual needing a shave form a coating which becomes a foamy gel as the propellant evaporates. This gel has good shaving characteristics and does not irritate the skin. The compositions are as follows:

Example 3
- 16 Copolymer #1
- 3 Ethyl Alcohol
- 1 Lauric Diethanolamide
- 60 Water
- 20 Dimethyl Ether (Propellant)
- 100

Example 4
- 15 Copolymer #3
- 10 Ethyl Alcohol
- 1 Lanolin Alcohol
- 39 Water
- 35 Isobutane (Propellant)
- 100

Example 5
- 18 Copolymer #1
- 2 Isopropyl Myristate
- 1 Lanolin
- 3 Isopropyl Alcohol
- 66 Water
- 10 Pentane (Propellant)
- 100

Example 6
- 20 Copolymer #4
- 2 Isopropyl Palmitate
- 1 Dimethyl Polysiloxane
- 3 Ethyl Alcohol
- 50 Water
- 24 Freon 115 Propellant
- 100

Example 7

-continued

| | |
|---|---|
| 15 | Copolymer #1 |
| 3 | Glyceryl Stearate |
| 2 | n-propanol |
| 65 | Water |
| 15 | Freon C-318 Propellant |
| 100 | |

Example 8

| | |
|---|---|
| 13 | Copolymer #1 |
| 20 | Glycerin |
| 7 | Freon 115 propellant |
| 50 | Water |
| 10 | Ethyl Alcohol |
| 100 | |

In the above Examples:

Copolymer #3 is a polyoxethylene-polyoxypropylene block copolymer of the type shown in formula (II) above having a polyoxypropylene hydrophobe molecular weight of 3250 and containing oxyethylene groups in amount of 50 percent of the total copolymer weight.

Copolymer #4 is a polyoxyethylene-polyoxypropylene block copolymer of the type shown in formula (II) above having a polyoxypropylene hydrophobe molecular weight of 3250 and containing oxyethylene groups in amount of 80 percent of the total copolymer weight.

EXAMPLE 9

A solution comprising 20 parts of copolymer #1, 4.0 parts of isopropanol, 2 parts of 150 molecular weight polyethylene glycol, 3 parts acetylated lanolin alcohol, 0.7 parts of fragrance, 1.0 part of 90 molecular weight polyethylene glycol, 0.2 part D&C Yellow No. 10 dye, 0.1 part F.D.&C Blue No. 1 dye, 2 parts specially denatured ethyl alcohol, and 67.1 parts water is prepared.

One hundred parts of the above liquid are placed in an aerosol container, the container is pressurized and sealed with a valve and 50 parts of isobutane propellant added through the valve. The contents when shaken and sprayed onto a human face having a growth of beard form a coating which becomes a foamy gel as the propellant evaporates. The beard is softened for shaving without irritating the skin.

The embodiments in which an exclusive privilege or property is claimed are defined as follows:

1. An aerosol shave cream composition comprising by weight about 35 to 85 percent water, about 1 to 10 percent volatile solvent, about 3 to 50 percent propellant and about 10 to 25 percent of a polyoxyethylene-polyoxypropylene copolymer of the formula:

$$Y[(C_3H_6O)_n(C_2H_4O)_mH]_x$$

wherein Y is the residue of a water-soluble organic compound containing therein x active hydrogen atoms; n is an integer; x is an integer greater than 1; the value of n and x are such that the molecular weight of the oxypropylene groups is from about 2250 to 7500; and the value of m is such that the oxyethylene groups constitute about 45 to 90 percent by weight of the compound and wherein the water/copolymer weight ratio is less than about 4.5:1.

2. The composition of claim 1 wherein Y is a propylene glycol residue whereby the resulting compounds have the structure $HO(C_2H_4O)_m(C_3H_6O)_n(C_2H_4O)_mH$ wherein n has a value such that the molecular weight of the poloxypropylene hydrophobe base is about 2250 to 4500 and m is the same as for claim 1.

3. The composition of claim 2 including about 0.05 to 5.0 percent treatment agent.

4. The composition of claim 3 including about 1.0 to 20.0 percent of at least one adjuvant.

5. The composition of claim 1 wherein Y is a residue of ethylene diamine whereby the resulting compounds have the structure:

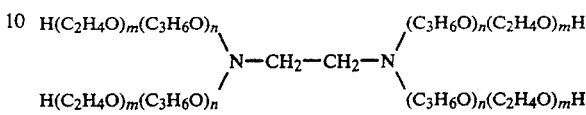

wherein n has a value such that the molecular weight of the polyoxypropylene hydrophobe base is about 3500 to 7500 and m is the same as for claim 1.

6. The composition of claim 5 including about 0.05 to 10.0 percent treatment agent.

7. The composition of claim 6 including about 1.0 to 20.0 percent of at least one adjuvant.

8. A pressurized shave cream composition in an aerosol container and adapted to form a spray upon release of pressure therefrom which composition is a liquid inside the container and forms a gel on contact with living tissue comprising by weight about 35 to 85 percent water, about 1 to 10 percent volatile solvent, about 3 to 50 percent propellant and about 10 to 25 percent of a polyoxyethylenepolyoxypropylene copolymer of the formula:

$$Y[(C_3H_6O)_n(C_2H_4O)_mH]_x$$

wherein Y is the residue of a water-soluble organic compound containing therein x active hydrogen atoms; n is an integer; x is an integer greater than 1; the values of n and x are such that the molecular weight of the oxypropylene groups is from about 2250 to 7500; and the value of m is such that the oxyethylene groups constitute about 45 to 90 percent by weight of the compound and wherein the water/copolymer weight ratio is less than about 4.5:1.

9. The composition of claim 8 wherein Y is a residue of propylene glycol whereby the resulting compounds have the structure $HO(C_2H_4O)_m(C_3H_6O)_n(C_2H_4O)_mH$ wherein n has a value such that the molecular weight of the polyoxypropylene hydrophobe base is about 2250 to 4500 and m is the the same as for claim 1.

10. The composition of claim 9 including about 0.05 to 10.0 percent by weight skin treatment agent.

11. The composition of claim 10 including about 1.0 to 20.0 percent of at least one adjuvant.

12. A process for applying a shaving cream to the skin comprising subjecting a gel composition to an elevated pressure in an aerosol container whereby said gel composition is a liquid, spraying said composition onto the skin, whereby a gel is formed on contact therewith, said composition comprising by weight about 35 to 85 percent water, about 1 to 10 percent by weight volatile solvent, about 3.0 to 50 percent propellant and about 10 to 25 percent of a polyoxyethylene-polyoxypropylene copolymer of the formula $$Y[(C_3H_6O)_n(C_2H_4O)_mH]_x$$

wherein Y is the residue of a water-soluble organic compound containing therein x active hydrogen atoms; n is an integer; x is an integer greater than 1; the value of n and x are such that the molecular weight of the oxypropylene groups is from about 2250 to 7500; and the value of m is such that the oxyethylene groups constitute about 45 to 90 percent by weight of the compound and wherein the water/copolymer weight ratio is less than about 4.5:1.

13. The process of claim 12 wherein said copolymer Y is a residue of propylene glycol whereby the resulting compounds have the structure $HO(C_2H_4O)_m(C_3H_6O)_n(C_2H_4O)_mH$ wherein n has a value such that the molecular weight of the polyoxypropylene hydrophobe base is about 2250 to 4500 and m is the same as for claim 1.

14. The process of claim 13 wherein said gel composition includes about 0.05 to 10.0 percent by weight skin treating agent.

15. The process of claim 14 wherein said gel composition includes about 1.0 to 20 percent of at least one adjuvant.

16. An apparatus for applying shaving cream to the skin comprising an aerosol container adapted to hold a material under pressure, a gel composition provided inside said container which is liquid when under the pressure normally found inside an aerosol container and which gels on contact with living skin, a valve adapted to close off or release the liquid under pressure in the form of a spray, said gel composition comprising by weight about 35 to 85 percent water, about 1 to 10 percent volatile solvent, about 3 to 50 percent of a propellant and about 10 to 25 percent polyoxyethylene-polyoxypropylene copolymer of the formula:

$$Y[(C_3H_6O)_n(C_2H_4O)_mH]_x$$

wherein Y is the residue of a water-soluble organic compound containing therein x active hydrogen atoms; n is an integer; x is an integer greater than 1; the value of n and x are such that the molecular weight of the oxypropylene groups is from about 2250 to 7500; and the value of m is such that the oxyethylene groups constitute about 45 to 90 percent by weight of the compound and wherein the water/copolymer ratio is less than about 4.5:1.

17. The apparatus of claim 16 wherein said copolymer Y is a residue of propylene glycol whereby the resulting compounds have the structure $HO(C_2H_4O)_m(C_3H_6O)_n(C_2H_4O)_mH$ wherein n has a value such that the molecular weight of the polyoxypropylene hydrophobe base is about 2250 to 4500 and m is the same as in claim 1.

18. The apparatus of claim 17 wherein said gel composition includes about 0.05 to 5 percent skin treating agent.

19. The apparatus of claim 18 wherein said gel composition includes about 1.0 to 20.0 percent of at least one adjuvant.

* * * * *